United States Patent [19]
Lorenz et al.

[11] Patent Number: 5,284,844
[45] Date of Patent: Feb. 8, 1994

[54] BIOCIDES FOR PROTECTING INDUSTRIAL MATERIALS AND WATER SYSTEMS

[75] Inventors: Joachim Lorenz; Reinhardt Grade, both of Bensheim, Fed. Rep. of Germany; Peter Riebli, Buckten, Switzerland

[73] Assignee: FMC Corporation, Philadelphia, Pa.

[21] Appl. No.: 411,335

[22] Filed: Sep. 22, 1989

[30] Foreign Application Priority Data

Sep. 30, 1988 [CH] Switzerland .................. 3636/88

[51] Int. Cl.$^5$ ............................................. A01N 43/00
[52] U.S. Cl. .................................................. 514/222.5
[58] Field of Search ............... 544/8; 514/222.5, 518; 252/106, 314; 8/490; 210/754, 755, 699; 106/15.05; 162/161; 71/67

[56] References Cited

U.S. PATENT DOCUMENTS

| | | | |
|---|---|---|---|
| 3,864,253 | 2/1975 | Shema | 514/518 |
| 4,010,110 | 3/1977 | Cosentino et al. | 252/314 |
| 4,022,605 | 5/1977 | Konya et al. | 71/67 |
| 4,097,594 | 6/1978 | Peake et al. | 514/222.5 |
| 4,143,138 | 3/1979 | Peake et al. | 514/222.5 |
| 4,201,780 | 5/1980 | Peake et al. | 514/222.5 |
| 4,295,932 | 10/1981 | Pocius | 162/161 |
| 4,450,269 | 5/1984 | Peake et al. | 544/8 |
| 4,462,820 | 7/1984 | Grade et al. | 71/67 |
| 4,497,807 | 2/1985 | Portnoy | 514/222.5 |
| 4,935,153 | 6/1990 | Favstritsky et al. | 210/755 |

FOREIGN PATENT DOCUMENTS

1577055 10/1980 United Kingdom .

OTHER PUBLICATIONS

Recl. Trav. Chim. Pays Bas., vol. 93, p. 270 (1974).
The Condensed Chem. Dictionary 10th Edition p. 130 (1981).

Primary Examiner—Frederick E. Waddell
Assistant Examiner—K. Weddington
Attorney, Agent, or Firm—Patrick C. Baker; Robert L. Andersen

[57] ABSTRACT

3,5-Dihalogeno-1,2,6-thiadiazin-4-ones of the formula

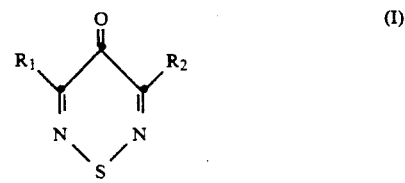

in which $R_1$ and $R_2$ independently of one another are chlorine, fluorine or bromine, in particular 3,5-dichloro-1,2,6-thiadiazin-4-one, are excellently suitable for use as biocides for the protection of industrial materials and for water systems, for example for wood, plastics, paints, oils, adhesives and industrial water circulation systems.

25 Claims, 1 Drawing Sheet

BIOCIDES FOR PROTECTING INDUSTRIAL MATERIALS AND WATER SYSTEMS

The present invention relates to the use of 3,5-dihalogeno-1,2,6-thiadiazin-4-ones, in particular 3,5-dichloro-1,2,6-thiadiazin-4-one, as biocides in the protection of materials and in water systems, to a process for protecting these materials and systems from harmful organisms and to these materials and systems containing the thiadiazinone derivatives defined above.

3,5-Dichloro-1,2,6-thiadiazin-4-one and a process for its preparation are described in Recl. Trav. Chim. Pays Bas 93, 270 (1974). U.S. Pat. No. 4,097,594 teaches that this compound and also 3-chloro-1,2,6-thiadiazinones carrying, however, other substituents in the 5-position instead of the chlorine atom, can be employed for the control of phytopathogenic fungi. U.S. Pat. Nos. 4,497,807, 4,143,138 and 4,201,780 also describe such 1,2,6-thiadiazinone derivatives which are not substituted by chlorine in the 5-position as plant fungicides.

GB-A 1,577,055 describes 3,5-dichloro-1,2,6-thiadiazinone and also corresponding compounds in which the chlorine atom in the 5-position is replaced by other substituents, as active ingredients in pharmaceutical compositions having an antimycotic and antibacterial activity and also as herbicides. It can be deduced from the equivalent DE-A 2,619,090 that the thiadiazinones which are not substituted by chlorine in the 5-position are to be regarded as preferred compared with the 3,5-dichloro derivatives in regard to their effectiveness. From none of the publications mentioned above can an indication be found that 3,5-dihalogeno-1,2,6-thiadiazin-4-ones can be employed as biocides in the protection of industrial materials or in water systems.

It has now been found, surprisingly, that 3,5-dihalogeno-1,2,6-thiadiazinones (in particular 3,5-dichloro-1,2,6-thiadiazinone) are not only excellently suitable for use as biocides for the protection of industrial materials and water systems, but also that they are even superior in effectiveness in this application to the other thiadiazinone derivatives described in the above publications, contrary to the teaching given there.

The present invention therefore relates to the use of 3,5-dihalogeno-1,2,6-thiadiazin-4-ones of the formula

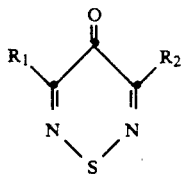

(I)

in which $R_1$ and $R_2$ independently of one another are chlorine, fluorine or bromine, as biocides in industrial materials and in water systems.

Figure 1:
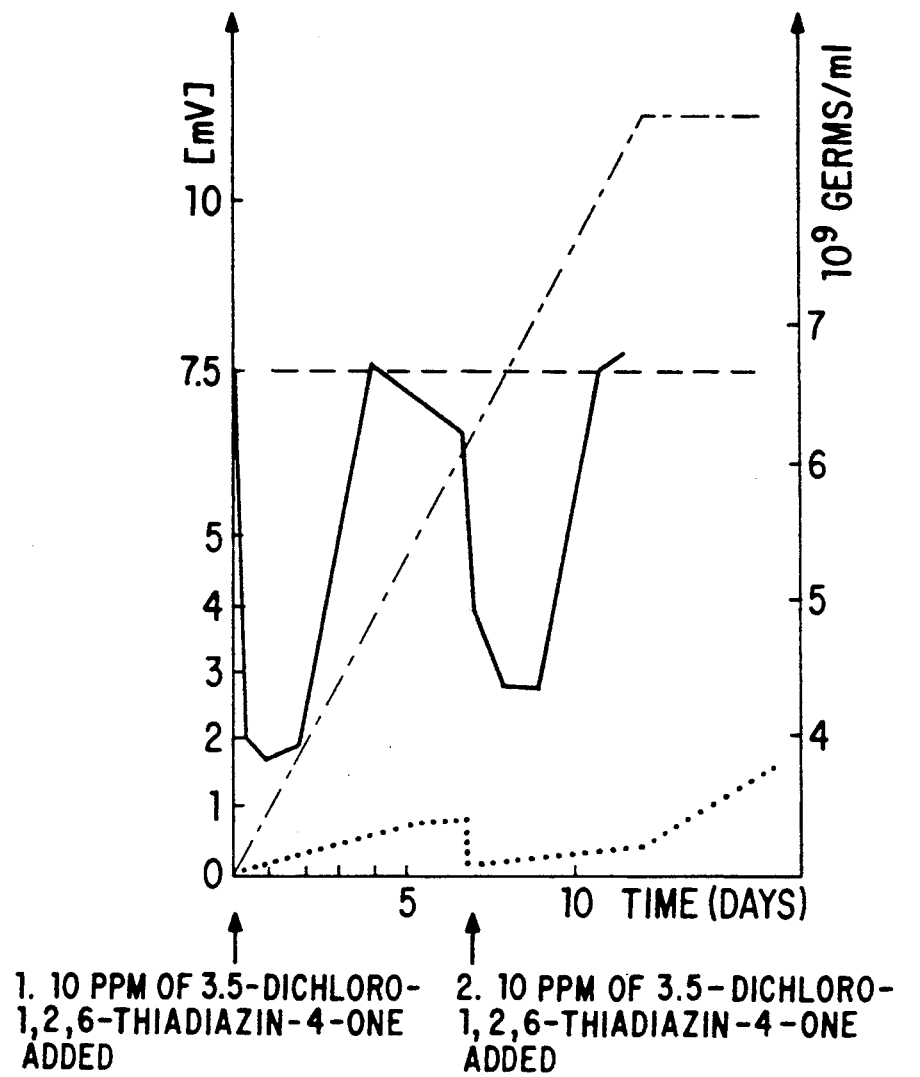
FIG. 1 is a plot of bactericidal test results based on reduced settlement of microorganisms in circulation systems, as described in Examples 3 and 4.

3,5-Dichloro-1,2,6-thiadiazinone is preferred for use in accordance with the invention; it is known from the publications mentioned above, as are also processes for its preparation. The other compounds of the formula I can be prepared analogously as described for the dichloro derivative in Trav. Chim. 93, 270 (1974), from the corresponding halogen-substituted starting compounds, insofar as the corresponding sulfur dihalides are available. Such compounds are, however, obtained in a particularly suitable manner from 3,5-dichloro-1,2,6-thiadiazin-4-one by halogen replacement reactions which are customary in chemistry. These reactions can, for example, be carried out by reacting the above compound with alkali metal fluorides or bromides, for example with NaF or NaBr, preferably in solvents suitable for this purpose or by means of a phase transfer catalyst. If unsymmetrical products of the formula I are desired, it is possible to replace only one chlorine atom by fluorine or bromine at a low temperature. The replacement of the second chlorine atom only takes place at a higher temperature.

The compounds of the formula

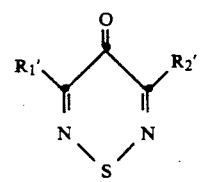

(IA)

in which $R_1'$ and $R_2'$ independently of one another are chlorine, fluorine or bromine, but are not both chlorine at the same time, are novel and are also a subject of the present invention.

The compounds of the formula I display a particularly high effectiveness against harmful organisms which attack industrial materials and water systems. Their very high activity against bacteria is particularly striking. However, their action against fungi and algae can also be described as very good.

Examples which may be mentioned of materials which can be protected by the biocides of the formula I are wood, cellulose, paper, plastics, coatings (for example paints), dyes (dye formulations), petroleum, motor fuels, drilling and cutting oils, lubricants, fats, waxes, textiles, leather, glass, rubber and adhesives and also industrial water circulation systems.

The use of the biocides of the formula I is particularly suitable for wood, plastics, paints, lacquers and industrial water circulation systems, in particular for wood, articles made of polyvinyl chloride, emulsion paints and anti-fouling paints.

The action of the compounds which can be used in accordance with the invention can be made use of advantageously in imparting a preservative and disinfectant finish to plastics, for example polyamides, polyurethane foams or polyvinyl chloride. If plasticizers are used, it is advantageous to add the antimicrobial additive, dissolved or dispersed in the plasticizer, to the plastic. The plastics having an antimicrobial finish can be used for utensils of all kinds in which it is desirable to have activity against a wide variety of germs, such as bacteria and fungi, for example in plasticized PVC films, for foot mats, bathroom curtains, toilet seats, grating walkways in swimming pools, wall coverings etc.

If paints (coating formulations) are protected, these are preferably emulsion paints and anti-fouling paints. As the binder, these contain, for example, the paint raw materials known to those skilled in the art, such as natural and synthetic resins, homopolymeric and copolymeric products containing the monomers vinyl chloride, vinylidene chloride, styrene, vinyltoluene, vinyl esters, acrylic acid and methacrylic acid, and also esters thereof, and chlorinated rubber, natural and synthetic rubber, if appropriate chlorinated or cyclized, and also reactive resins, such as epoxy resins, polyurethane resins and unsaturated polyesters, which can, if desired, be converted into film-forming products of fairly high molecular weight by the addition of curing agents.

When used for protecting timber, particular use is made of the excellent action of the compounds of the formula I against the fungi and bacteria which cause the rotting of timber. It is preferable to treat the timber to be protected with a formulation (for example a timber protective stain) containing the compound of the formula I. In this way it is possible to protect, for example, building materials made of timber, and also buildings consisting wholly or partly of timber. In particular, the compounds of the formula I are very active against blue stain fungi and mould fungi in the temporary protection of timber, i.e. they are particularly suitable for the treatment of green timber.

The use of the compounds of the formula I as biocides in water systems should be singled out particularly. In particular, the compounds are suitable for preventing or reducing the formation of slime in water systems, for example in industrial water circulation systems, for example in cooling circulation systems.

In general, the following water systems inter alia can be protected by means of the biocides of the formula I:

Industrial cooling water, for example for power stations or chemical plants, for steel and paper factories and for breweries. These can be closed or open circulation systems, for example with cooling towers; also process effluents, particularly those containing nutrients for micro-organisms, for example effluent from paper factories and breweries; and also injected water for oil fields or water employed in reverse osmosis processes, for example in industrial uses or for boiler water.

Other water systems in which the compounds of the formula I can be employed are circulation water in the paper industry, cooling water in fertilizer manufacture, in oil refineries, in the manufacture of metals (for example steel and copper), in the petrochemical and rubber-manufacturing industries and in the textile and fibre industry, in gas production, in the processing of minerals, in the production of glass, ceramics, food and leather, in heavy and light industry, including the manufacture of metals and automobiles, in furniture manufacture, in the electronics industry, in the paint and adhesives industry and in other manufacturing plants.

Further fields of application relate to the treatment of geothermal water, of water in central heating systems and air conditioning systems in private, public or industrial buildings, of water for hydrostatic tests on pipelines and vessels, of water for swimming pools and of cooling water for ships machinery, and also the treatment of industrial ponds.

Further customary auxiliaries, for example corrosion inhibitors, boiler scale inhibitors, water softening agents, sequestering agents, for example polymeric phosphites, phosphates, amides of phosphoric acid, phosphonic acids and polymeric carboxylic acids derived from, for example, acrylic acid or maleic acid, anhydrides or salts thereof and other additives, can be added at the same time when the compounds of the formula I are used in accordance with the invention, particularly in the control of harmful organisms in water systems, such as water circulation systems (for example in cooling water systems).

The use of the compounds of the formula I as biocides is of particular practical importance in industrial water circulation systems, swimming pools and industrial ponds; in cooling water and process water, particularly cooling water in power stations, chemical plants, steel or paper factories, breweries, ships or seawater machinery; in injection water for oil fields; and in geothermal water or water in central heating or air-conditioning systems or in water for hydrostatic tests.

A further field of application for the present invention is disinfection of surfaces. These can be made of a very wide variety of materials, for example of wood, plastics, metal etc. Surfaces of furniture and utensils in hospitals should be mentioned particularly.

The present invention also relates to a process for protecting industrial materials and water systems from attack by harmful organisms or for controlling the latter on or in industrial materials and water systems, which comprises incorporating in or applying to the said materials or systems a compound of the formula I, in particular 3,5-dichloro-1,2,6-thiadiazin-4-one. The invention further relates to said materials and water systems which contain a compound of the formula I. Preferred industrial materials and water systems are indicated above in the illustration of the use, in accordance with the invention, of the compounds of the formula I.

The amount of compounds of the formula I which is added to or applied to the water systems and the industrial materials depends, of course, largely on the particular mode of application, and can therefore vary within wide limits. Owing to the excellent effectiveness of the compounds of the formula I, lower concentrations can be found sufficient, in comparison with analogous agents, as a result of which particularly advantageous ecological aspects result.

Depending on their end use, the compounds are employed in the ranges of concentration which are known to those skilled in the art. Whereas concentrations as low as the ppm range are sufficient in water systems (cooling water etc), concentrations of up to 40% by weight are customary in anti-fouling formulations.

Owing to the broad spectrum of use, examples of suitable concentrations of the compound of the formula I are 0.1 ppm to 40% by weight, relative in each case to the substrate to be treated. Typical concentrations in timber preservatives are 0.01 to 10% by weight, in particular 0.1 to 5% by weight, approximately the same amount in finishes for plastics, for example plasticized PVC films, 0.1–40, in particular 0.5 to 20, for example 0.5 to 10, % by weight in paints, for example emulsion and anti-fouling paints, 0.01–5, in particular 0.01–1, % by weight in petroleum, motor fuels, oils, fats, waxes, drilling and cutting oils, lubricants and the like, and 0.01 to 1000, preferably 0.05 to 100, in particular 0.05 to 50, for example 1–40, but also 0.01–5, ppm in water systems, as in cooling circulation systems and the like.

The compounds of the formula I can be applied in the pure form or together with carriers, for example formulation assistants. They can also be suspended in liquid coating agents and the like, in which regard, if appropriate, wetting agents or emulsifiers can promote the uniform distribution of the active ingredient in order to form uniform dispersions. It is also possible to add other biocides.

To sum up, some important fields of application for the compounds of the formula I will be listed again. The latter are suitable, for example, as already mentioned, as preservatives for industrial solutions, as additives to building materials, preferably to mortars, renderings (interior rendering, external rendering, flooring plaster and the like) or to mixtures containing hydraulic binders, such as concrete, as additives to metal machining fluids, preferably to drilling and cutting oils, and also to rolling materials, forging materials, separating materials and lubricants, as an additive to coating materials, suitably to paints and lacquers and preferably emulsion paints, as an active medium in coatings which inhibit or prevent rotting, so-called antifouling coatings, for imparting a biocidal finish to surface coatings generally and to timber, plastics, polymeric materials, paper, leather and textiles, for the surface treatment of or for incorporation in building materials and building components made of polymeric material, as an anti-slime agent in water systems, preferably in systems for cooling water, and in process water, in particular in the cellulose-processing industry, such as the paper industry, and finally for disinfection.

In addition to use in water systems, where, in particular, an extremely good effect can be observed against the slime formation caused by bacteria, another preferred field of use is that in protective coating materials, in particular in anti-fouling paints which, in addition to the customary base materials and additives, contain, for example, 0.5-40% by weight, preferably 3 to 15% by weight, relative to the total mixture, of at least one compound of the formula I.

Customary base materials for anti-fouling paints are the paint raw materials described as binders and known to those skilled in the art, such as natural and synthetic resins, homopolymeric and copolymeric products containing the monomers vinyl chloride, vinylidene chloride, styrene, vinyltoluene, vinyl esters, vinyl alcohols, acrylic acid and methacrylic acid and esters thereof, polyester resins and polyamide resins, and also chlorinated rubber, natural and synthetic rubber, if appropriate chlorinated or cyclized, and also reactive resins, such as epoxy resins, polyurethane resins and unsaturated polyesters, which can, if appropriate, be converted into film-forming products of fairly high molecular weight by the addition of curing agents.

The binders can be liquid or in a dissolved form. In the case of dissolved binders, also thermoplastics, a protective film can also be formed by evaporating the solvent. Solid coating agents can, for example, be applied to articles by the powder coating process. Examples of other customary base materials are tar, modifiers, dyes, inorganic or organic pigments, fillers and curing agents.

Finally, the compounds of the formula I can also be used in elastomeric coatings and also in silicone elastomers and polymers containing fluorine.

In industry, active ingredients are often employed in combination with other biocides. The compounds of the formula I can also be combined with other biocides. Combinations of products often prove advantageous in the case of anti-fouling paints. Thus the compounds according to the invention can be combined with, for example, $Cu_2O$, CuSCN, zinc oxide, triorganotin compounds, such as tributyltin fluoride or triphenyltin chloride, metallic copper or triazines or, in general, with compounds known to those skilled in the art as effective against animal or vegetable growth.

A further form in which the compounds of the formula I are used is incorporation in plastics or natural or synthetic rubbers, or application to the surfaces of shaped articles composed of these plastics, for example polyvinyl chlorides and copolymers and mixed polymers thereof, polyalkylenes, polyacrylates, polystyrenes, copolymers thereof, polyurethanes or polyisocyanates, polyesters, epoxy resins and the like.

Their use is particularly appropriate in the case of plastics or polymeric materials which are used as building materials and, for example, are exposed to weathering or are employed in the domain of moistening or wetting regions. It is possible to mention as examples of insulating materials against heat and cold, roofing materials or linings made of polyvinyl chloride, butyl rubber, chlorinated polyethylene, polyisobutylene, chloroprene and chloroisoprene, EPDM and also PVC copolymers containing vinyl acetate or ethylvinyl acetate, polyacrylonitrile/styrene, if appropriate as a mixture with fibrous fillers (if appropriate also as a blend with bitumen), or foamed polyvinyl chlorides or polystyrenes.

The compounds of the formula I are suitable for both the uses mentioned and also for other uses. They are non-hygroscopic and stable to heat and have a low solubility in water.

The invention also embraces compositions (formulations) containing at least one compound of the formula I. The form and nature of the particular composition containing the compound according to the invention depends on the end use.

For application the compounds of the formula I can be present in the following processing forms (in which the weight percentage data in the brackets represent advantageous amounts of active ingredient):

Solid processing forms: dusting compositions and sprinkling compositions (up to 10%) of granules, coated granules, impregnated granules and homogeneous granules and pellets (grains) (1 to 80%).

Liquid processing forms:
a) water-dispersible active ingredient concentrates: wettable powders and pastes (25-90% in the commercial pack, 0.01 to 15%, in a solution ready for use), emulsion concentrates and solution concentrates (10 to 50%; 0.01 to 15% in a solution ready for use);
b) Organic solutions (0.1 to 20%); aerosols.

The biocidal compositions can also contain other active substances, or the compounds of the formula I can also be employed together with other biocidal active ingredients in the types of use mentioned above.

The following are examples of such other biocidal active ingredients:

a) Organosulfur compounds, for example methylene dithiocyanate (MBT), isothiazolones or 3,5-dimethyltetrahydro-1,3,5-2-H-thiodiazine-2-thione (DMTT). Substances of this type are employed particularly against the formation of slime in paper manufacture.

b) Chlorinated phenols, such as sodium pentachlorophenate. Compounds of this type are distinguished by a very broad spectrum of action.

c) Copper salts, such as copper sulfate and copper nitrate, as additional algicides.

d) 2,2-Dibromo-3-nitrilopropionamide (DBNPA) as an algicide, fungicide and bactericide.

e) Chlorine and bromine as algicides and bactericides; these can be used particularly in the treatment of water.

f) Chlorine dioxide, chloroisocyanurates and hypochlorites as biocides; these can also be employed particularly in the treatment of water.

g) Triazines, for example 2-methylthio-4-t-butylamino-6-cyclopropylamino-s-triazine, particularly as algicides.

h) Triorganotin compounds, for example bis-tributyltin oxide (TBTO), in particular as fungicides and algicides.

i) Timber biocides ia) Salt mixtures based on silicofluorides, hydrogenfluorides, inorganic boron compounds, chromates, fluorides, arsenic (oxide or arsenates), copper salts (sulfate or naphthenate), tin and zinc salts and mercury compounds.

ib) ar oil preparations ic) Organic active ingredients, such as pentachlorophenol, phenol, DDT, dieldrin, lindane, gammexane, chlorinated naphthalenes, dichlorofluanide, tributyltin compounds, pyrethroids, 3-iodo-2-propenyl N-butylcarbamate and furmecyclox.

j) Disinfectants ja) Phenol or phenol derivatives jb) Formaldehyde and/or other aldehydes or derivatives jc) Chlorine or organic or inorganic substances containing active chlorine jd) Amphoteric surfactants je) Quaternary onium compounds.

Combinations of the thiadiazinones which can be used in accordance with the invention with other biocides, for example those of the above classes, can exhibit synergistic effects. Such effects occur particularly in combinations with amines, quaternary ammonium salts, isothiazolones and thiocyanates. Examples of these are combinations of 3,5-dichloro-1,2,6-thiadiazin-4-one with 1) coconut oil amine, 2) 5-chloro-2-methyl-4-isothiazolon-3-one/2-methyl-4-isothiazolon-3-one mixtures (for example 2.65:1), 3) dodecyl/tetradecyl-benzyldimethylammonium chloride and 4) methylene bisthiocyanate.

Other substances and assistants such as are customarily concomitantly used in such formulations can, of course, be present in addition in such formulations. These include, for example, anionic, cationic or nonionic surface-active substances, electrolytes, complex-formers, solubilizers and dyes and perfumes. These additives are used, for example, to improve the wetting power, the stability of curing, to adjust the viscosity and to increase the stability of the solutions in the cold.

When used in emulsion paints and emulsion renderings, the compounds of the formula I can, for example, also be combined with other fungicides. In water treatment combinations with a bactericide are possible in order to control slime-forming bacteria. Such combinations can afford advantages in technical performance. In many cases the combination with other algicides is also advantageous.

The invention also embraces compositions containing a) a coating material and b) an effective amount of at least one compound of the formula I.

As already mentioned, a particular advantage of the compounds of the formula I which can be used in accordance with the invention lies in the fact that the concentration in which they are used can be kept low, compared with products having a similar action. It is surprising that, in spite of these low concentrations of use, the compounds not only adequately inhibit the growth of harmful organisms, in particular bacteria, but also destroy them, as a result of which the compounds mentioned can also be employed very suitably for disinfection.

It is also surprising that, under conditions under which the compounds which can be used in accordance with the invention no longer have a growth-inhibiting action, or, for example, in water circulation systems even when the organisms (for example bacteria) can again propagate, settlement of the latter on the surfaces is prevented or at least greatly reduced by the compounds of the formula I. The compounds of the formula I therefore act even in very small concentrations (for example 0.01 to 10 ppm) as "deposit control agents", i.e. they prevent the settlement of microorganisms on the substrates which are intended to be protected (for example they prevent the formation of slime), although they are applied only in "sub-biocidal" amounts. The present invention also relates to this use of the compounds of the formula I and to a process for preventing the settlement of harmful organisms on industrial materials and water systems by means of such sub-biocidal amounts of compounds of the formula I.

The following examples illustrate the invention further, in particular they show the good activity of the compounds of the formula I. In these examples, just as in the remainder of the description and the patent claims, percentages and parts are by weight unless stated otherwise.

EXAMPLE 1

Determination of the minimal inhibition concentration (MIC) for six strains of bacteria MIC=minimal inhibition concentration, corresponds to the concentration of an active substance which is just sufficient to inhibit the growth of bacteria in a nutrient solution.

Strains which are obtained from "overnight cultures" ( a 24 -hour culture starting in each case from a colony on caso-peptone agar) are used:

| | Description | Source of supply and number | Germ count of the ONC/ml |
|---|---|---|---|
| A | Bacillus subtilis | ATCC 6051 | $1,3 \times 10^9$ |
| B | Serratia marcescens | ATCC 13880 | $4,0 \times 10^{10}$ |
| C | Enterobacter aerogenes | ATCC 13048 | $1,6 \times 10^{10}$ |
| D | Alcaligenes denitrificans | ATCC 15173 | $1,3 \times 10^{10}$ |
| E | Proteus vulgaris | ATCC 13315 | $2,4 \times 10^{10}$ |
| F | Pseudomonas aeruginosa | ATCC 10145 | $1,8 \times 10^{10}$ |

ONC = overnight culture 100 mg of the substance to be tested are dissolved in 5 ml of dimethylformamide. Sufficient of this solution to give concentrations of 3, 10, 30, 100 and 300 ppm of the substance to be tested in the nutrient solution are added in each case to caso-peptone broth which has been inoculated with the particular ONC. The test tubes containing the inoculated nutrient solution are incubated at 30° C. for 24 hours in a shaking bath, and the growth or non-growth of the bacteria is then evaluated. The MIC values thus determined (in mg/l) are collated in Table 1.

TABLE 1

| Strains | MIC (mg/l) | | | | | |
|---|---|---|---|---|---|---|
| | A | B | C | D | E | F |
| Substance tested 3,5-dichloro-1,2,6-thiadiazin-4-one | 10 | 3 | 10 | 3 | 3 | 3 |

EXAMPLE 2

Determination of the "Minimal Concentration Required to Kill a Bacterial Culture" (MKC Mixed Culture)

MKC=minimal killing concentration, corresponds to the concentration of an active substance which is just sufficient to kill the bacteria in a buffer solution.

Strains which are obtained from "overnight cultures" (a 24-hour culture starting in each case from a colony on caso-peptide agar) are used:

|   | Description | Source of supply and number | Germ count of the ONC/ml |
|---|---|---|---|
| G | Escheria coli | ATCC 4157 | $1.0 \times 10^{10}$ |
| H | Bacillus cereus var. mycoides | DSM 299 | $3.6 \times 10^{8}$ |
| I | Staphylococcus aureus | ATCC 6538 P | $4.5 \times 10^{9}$ |
| C | Enterobacter aerogenes | ATCC 13048 | $1.6 \times 10^{10}$ |
| E | Proteus vulgaris | ATCC 13315 | $2.4 \times 10^{10}$ |
| F | Pseudomonas aeruginosa | ATCC 10145 | $1.8 \times 10^{10}$ |

ONC = overnight culture 0.5 ml of each of the ONCs in the above table are together thoroughly shaken in an Erlenmeyer flask. The mixed culture thus obtained is added to a Tyrode solution in such a quantity that a germ count of $10^7$ or $10^6$ or $10^5$ germs/ml is obtained. The substance to be tested is then added in the desired test concentration and the mixture is incubated for 5 hours at 30° C. 5 μl of the cultures thus treated are added dropwise to caso-agar plates and incubated at 30° C. for 24 hours; the plates are then assessed to determine growth or mortality of the bacteria.

TABLE 2

| 3,5-Dichloro-1,2,6-thiadiazin-4-one added in a concentration of | Germ count/ml | | |
|---|---|---|---|
|  | $10^7$ | $10^6$ | $10^5$ |
|  | Assessment | | |
| 6 mg/l | (+) | — | — |
| 10 mg/l | — | — | — |
| 30 mg/l | — | — | — |
| 60 mg/l | — | — | — |
| 100 mg/l | — | — | — |
| 0 mg/l (growth control) | + | + | + |

Assessment scheme:
+Growth of bacteria, no mortality
(+)Bacterial growth, but slight mortality (>10 colonies)
(−)Appreciable mortality of bacterial growth (≦10 colonies)
−Complete mortality, no growth visible (0 colonies)

EXAMPLE 3

Determination of Settlement in a Growing Culture

Stainless steel cylinders are put into a growing culture of Pseudomonas fluorescens and the settlement on the surface is determined by measuring the ATP content (adenosine triphosphate, expressed in millivolts (mV)) by means of known heat extraction processes and bioluminescence. At the same time the ATP content of the cells in the medium is investigated. If the ATP content of the cells in the medium has not declined and if the content of ATP extract from the cylinder is low, this means that the cells were not able to form a deposit on the metal surface. The ATP content is measured before the addition of the compound to be tested, 3,5-dichloro-1,2,6-thiadiazin-4-one. The compound to be tested is then added in a concentration of 5 mg/l and the ATP content is determined again 30 minutes after this addition (in the medium and on the cylinder). A sample not treated with 3,5-dichloro-1,2,6-thiadizin-4-one is used as a comparison. The treatment with the compound to be tested is carried out 2× (test 1 and test 2). The results can be seen in Table 3.

TABLE 3

| Additive | ATP in the medium (mV) $T_0$ | ATP in the medium (mV) $T_1$ | ATP on the cylinder (mV) |
|---|---|---|---|
| 5 mg/l 3,5-dichloro-1,2,6-thiadiazin-4-one (test 1) | 1,66 | 2,98 | 1,20 |
| 5 mg/l 3,5-dichloro 1,2,6-thiadiazin-4-one (test 2) | 4,40 | 6,78 | 1,51 |
| no additive (comparison sample) | 2,10 | 4,92 | 2,39 |

ATP in the medium ($T_0$) = before the addition of substance
ATP in the medium ($T_1$) = 30 minutes after the addition of substance
ATP on the cylinder = 30 minutes after the addition of substance.

As can be seen from the table, the ATP content on the cylinders has, surprisingly, been reduced in contrast with the comparison by the addition of 3,5-dichloro-1,2,6-thiadiazin-4-one, although the ATP concentration in the medium (at varying initial ATP contents) increases further after the addition of the product, i.e. under these conditions 5 ppm of the test substance do not yet have a biocidal action. In spite of the low concentration employed, the test substance reduces the settlement of Pseudomonas fluorescens.

EXAMPLE 4

Determination of the Settlement of Microorganisms in Circulation Systems

The circulation systems located in the area consist of:
a) a plastic drum having a volume of 113 l
b) a pump (21 l/minute at a delivery height of 3 m)
c) a cooling tower fitted with Oregon (splint) plates, Oregon (heart wood) plates, oak plates, spruce plates and PVC plates.

Fresh water is only added to make up for water removed by evaporation. The circulation systems are infested by the natural entry of dust and not by deliberate inoculation.

The circulation system is treated twice with 10 ppm of the test substance (3,5-dichloro-1,2,6-thiadiazin-4-one) in order to prevent the settlement of bacteria.

The test is evaluated by determining the germ titre by dilution and scraping out with a spatula and by measuring the settlement on steel cylinders hung in the drums. The settlement is determined by measuring the ATP content on the cylinders using a known heat extraction process and bioluminescence (see Example 3). The results obtained can be seen from FIG. 1.

The excellent action of the test substance (3,5-dichloro-1,2,6-thiadiazin-4-one) can be seen from the curves in FIG. 1. 10 ppm of the product kill most of the bacteria in the circulating system (germ count reduced by a power of 5) and hence settlement does not take place either. The growth-inhibiting action dies away after 3 days. Surprisingly, however, in spite of bacterial growth, virtually no settlement takes place on the cylinders.

EXAMPLE 5

Determination of the Minimal Inhibition Concentration (MIC) for Algae

Cultures of the following strains of algae

J—*Oscillatoria geminata*
K—*Nostoc spez.*
L—*Phormidium foveolarum*
M—*Chlorella vulgaris*
N—*Scenedesmus spec.*
O—*Ulothrix subtilissima*
P—*Tribonema aequale* grown in an algae nutrient medium for 14 days are diluted in the algae nutrient medium by a factor of 1:100 or 1:200. The suspensions are added dropwise to algae agar containing 3,5-dichloro-1,2,6-thiadiazin-4-one in various concentrations (0.1, 0.3, 1, 3 and 10 mg/l). Growth is evaluated after incubation for 14 days at room temperature under an alternation of 14 hours light/10 hours darkness. The MIC values obtained can be seen in Table 4.

TABLE 4

| Alga | MIC (mg/l) | | | | | |
|---|---|---|---|---|---|---|
| | J | K | L | M | N | O | P |
| Substance tested 3,5-dichloro-1,2,6-thiadiazin-4-one | 0,3 | 0,1 | 0,1 | 0,1 | 3 | 0,1 | 0,1 |

EXAMPLE 6

Determination of the Minimal Inhibition Concentration (MIC) for Fungi

The following strains of fungi are used:
Q—*Aspergillus niger*
R—*Sacharomyces cerevisiae*
S—*Penicillium funiculosum*
T—*Chaetomium globosum*
U—*Aureobasidium pullulans*
V—*Coniophora puteana*

The test is carried out using the known agar incorporation test in malt extract agar. Inhibition is carried out by adding sufficient 3,5-dichloro-1,2,6-thiadiazin-4-one to give, respectively, concentrations of 10, 50 and 100 mg/l in the agar. The concentrations (mg/l) required to inhibit the growth of the fungi (starting from fungal spores added dropwise) are shown in Table 5.

TABLE 5

| Fungus | MIC (mg/l) | | | | | |
|---|---|---|---|---|---|---|
| | Q | R | S | T | U | V |
| substance tested 3,5-dichloro-1,2,6-thiadiazin-4-one | ≦10 | ≦10 | ≦10 | ≦10 | ≦10 | ≦10 |

EXAMPLE 7

Determination of Protective Action Against Fungal Attack in Freshly Sawn Timber

The tests are carried out analogously to the NWPC standard 1.4.1.3/79:
Mycological testing of anti-stain
Preservatives for freshly sawn timber
the mini-board method
NWPC-Standard 1.4.1.3/79

A 10% stock solution of 3,5-dichloro-1,2,6-thiadiazin-4-one is made up in the following mixture of solvents:
60% of phenyl polyethylene glycol ether
30% of polyethylene glycol oleate
10% of methanol.

This stock solution is diluted with water to give 0.01%, 0.02%, 0.025%, 0.05%, 0.1% and 0.2% stable emulsions.

Pine boards (10×50×300 mm) are immersed for half their length in the particular solution for 20 seconds, dried for 24 hours and inoculated with the following mixed cultures:

Test fungi:
1. "Blue stain fungi" mixed culture composed of
   *Aureobasidium pullulans*
   *Sclerophoma pityophila*
   *Ceratocystis pilifera*
2. "Mould" mixed culture composed of
   *Aspergillus niger*
   *Penicillium funiculosum*
   *Trichoderma viride*

The inoculated timber is incubated at room temperature and growth is assessed after 6 weeks on the basis of the following rating:
0 = no fungal growth
1 = traces of fungus
2 = some fungal growth
3 = moderate fungal growth
4 = considerable fungal growth.

The results obtained are collated in Table 6.

TABLE 6

| concentration of 3,5-dichloro-1,2,6-thiadiazin-4-one | Growth | | | |
|---|---|---|---|---|
| | untreated | | treated half | |
| 0,01% | 4 | 4 | 4 | 4 |
| 0,02% | 4 | 3 | 1 | 0–1 |
| 0,025% | 2 | 2 | 0 | 0 |
| 0,05% | 2 | 3 | 0 | 0 |
| 0,1% | 4 | 1–2 | 0 | 0 |
| 0,2% | 4 | 3 | 0 | 0 |

Two boards are treated in each case.

EXAMPLE 8

Determination of the "Minimal Concentration Required to Kill a Bacterial Culture" (MKC Mixed Culture)

MKC = minimal killing concentration, corresponds to the concentration of an active substance which is just sufficient to kill the bacteria in a buffer solution.

Strains obtained from "overnight cultures" (in each case a 24-hour culture starting from a colony on casopeptone agar) are used:

| | Description | Source of supply and number | Germ count of the ONC/ml |
|---|---|---|---|
| G | *Escheria coli* | ATCC 4157 | $1,0 \times 10^{10}$ |
| H | *Bacillus cereus* var. *mycoides* | DSM 299 | $3,6 \times 10^{8}$ |
| I | *Staphylococcus aureus* | ATCC 6538 P | $4,5 \times 10^{9}$ |
| C | *Enterobacter aerogenes* | ATCC 13048 | $1,6 \times 10^{10}$ |
| E | *Proteus vulgaris* | ATCC 13315 | $2,4 \times 10^{10}$ |
| F | *Pseudomonas aeruginosa* | ATCC 10145 | $1,8 \times 10^{10}$ |

ONC = overnight culture 0.5 ml of each of the ONCs in the above table are together thoroughly shaken in an Erlenmeyer flask. The mixed culture thus obtained is added to a Tyrode solution in such an amount that a germ count of $10^7$ or $10^6$ germs/ml is achieved. The substances to be tested are then added in the desired test concentrations and the mixtures are incubated for 5 hours and 24 hours at 30° C. 5 μl of the cultures thus treated are added dropwise to caso-agar plates and incubated at 30° C. for 24 hours; the plates are then assessed to determine growth or mortality of the bacteria.

Combinations of 3,5-dichloro-1,2,6-thiadiazin-4-one and other biocides are employed in this example.

As can be seen from Table 7 and 8 below, 3,5-dichloro-1,2,6-thiadiazin-4-one shows a synergistic effect with various biocides, for example coconut oil amine (dodecylamine), a 2.65:1 mixture of 5-chloro-2-methyl-4-isothiazolon-3-one and 2-methyl-4isothiazolon-3-one, a quaternary ammonium compound such as $C_{12}/C_{14}$alkylbenzyldimethylammonium chloride and methylene bisthiocyanate. The quantities of biocides employed and the results obtained can be seen in Tables 7 and 8.

TABLE 7

| Additive: | In a concentration of: | Germ count $10^6$ germs/ml Growth/number of colonies after ... hours (h) |
|---|---|---|
| a) coconut oil amine | 5 ppm | +5 h |
| | | (−)24 h (5 colonies) |
| b) 3,5-dichloro-1,2,6-thiadiazin-4-one | 3 ppm | (−)5 h (9 colonies) |
| | | (−)24 h (2 colonies) |
| a) + b) | 2 + 1 ppm | −5 h |
| | | −24 h |
| e) 5-chloro-2-methyl-4-isothiazolon-3-one + 2-methyl-4-isothiazolon-3-one (2.65:1) | 1 ppm | +5 h |
| | | +24 h |
| b) 3,5-dichloro-1,2,6-thiadiazin-4-one | 1 ppm | +5 h |
| | | +24 h |
| e) + b) | 0.5 + 0.5 ppm | +5 h |
| | | (−)24 h (1 colonies) |

TABLE 8

| Additive: | In a concentration of: | Germ count $10^7$ germs/ml Growth/number of colonies after ... hours (h) |
|---|---|---|
| a) coconut oil amine | 10 ppm | +5 h |
| | | +24 h |
| b) 3,5-dichloro-1,2,6-thiadiazin-4-one | 4 ppm | (−)5 h (2 colonies) |
| | | (−)24 h (8 colonies) |
| a) + b) | 2 + 2 ppm | −5 h |
| | | −24 h |
| c) dodecyl/tetradecyl-benzyldimethyl-ammoniumchloride | 10 ppm | +5 h |
| | | +24 h |
| b) 3,5-dichloro-1,2,6-thiadiazine-4-one | 5 ppm | (−)5 h (1 colonies) |
| | | (−)24 h (1 colonies) |
| c) + b) | 3 + 2 ppm | (−)5 h (5 colonies) |
| | | −24 h |
| f) methylene-bis-thiocyanate | 5 ppm | +5 h |
| | | (+)24 h |
| b) 3,5-dichloro-1,2,6-thiadiazin-4-one | 4 ppm | (−)5 h (2 colonies) |
| | | (−)24 h (8 colonies) |
| f) + b) | 2 + 2 ppm | (−)5 h (3 colonies) |
| | | −24 h |

Assessment rating:
+ bacterial growth, no mortality
(+) bacterial growth, but low mortality (>10 colonies)
(−) appreciable mortality of bacterial growth (≦10 colonies)
− complete mortality, no growth visible (0 colonies)

What is claimed is:

1. A process for protecting industrial materials and water systems from attack by harmful organisms or for controlling the latter on or in industrial materials and water systems, which comprises incorporating in or applying to the said materials or systems a 3,5-dihalogeno-1,2,6-thiadiazin-4-one of the formula I

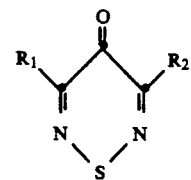

in which $R_1$ and $R_2$ independently of one another are chlorine, fluorine or bromine.

2. A process according to claim 1 wherein the compound of formula I is 3,5-dichloro-1,2,6-tiadiazin-4-one.

3. A process according to claim 1, wherein the industrial materials are selected from the group consisting of wood, cellulose, paper, plastics, paints, lacquers, drilling and cutting oils, petroleum, motor fuels, lubricants, fats and waxes, textiles, leather, glass, rubber and adhesives and the water systems are industrial water circulation systems.

4. A process according to claim 1 for protecting wood, plastics, paints and lacquers and industrial water circulation systems.

5. A process according to claim 4 for protecting wood, articles made of polyvinyl chloride and emulsion or anti-fouling paints.

6. A process according to claim 1 for protecting water systems.

7. A process according to claim 6, wherein the water system is an industrial water circulation system, a swimming pool or an industrial pond.

8. A process according to claim 6, wherein the water system is cooling water or process water.

9. A process according to claim 8, wherein the water system is cooling water in power stations, chemical plants, steel or paper factories, breweries, ships or seawater machinery.

10. A process according to claim 6, wherein the aqueous system is injection water for oil fields.

11. A process according to claim 6, wherein the water system is geothermal water, water in central heating systems or air-conditioning systems or water for hydrostatic tests.

12. A process according to claim 1 for disinfecting surfaces.

13. A process according to claim 1, wherein the thiadiazinone is employed in an amount of 0.0001 to 40% by weight, relative to the industrial materials or water systems.

14. A process according to claim 1, wherein at least one further biocide is added.

15. Industrial materials and water systems containing, as the biocide, a 3,5-dihalogeno-1,2,6-thiadiazin-4-one of the formula I.

16. An industrial material according to claim 15 selected from the group consisting of wood, cellulose, paper, plastics, paints, lacquers, drilling and cutting oils, petroleum, motor fuels, lubricants, fats, waxes, textiles, glass, rubber and adhesives.

17. An industrial material according to claim 16 selected from the group consisting of wood, plastics, paints and lacquers.

18. An industrial material according to claim 17 selected from the group consisting of wood, articles made of polyvinyl chloride, and emulsion or antifouling paints.

19. A water system according to claim 15 selected from the group consisting of industrial water circulation systems, swimming pools and industrial ponds.

20. A water system according to claim 15 selected from the group consisting of cooling water and process water.

21. A water system according to claim 20 selected from the group consisting of cooling water in power stations, chemical plants, steel or paper factories, breweries, ships and seawater machinery.

22. A water system according to claim 15 selected from the group consisting of geothermal water, water in central heating systems, and water for hydrostatic tests.

23. A water system according to claim 15 which is injection water for oil fields.

24. A material and a system according to claim 15, which contain at least one further biocide.

25. A process for preventing the settlement of harmful organisms on industrial materials and water systems, which comprises incorporating in or applying to the said materials or systems a sub-biocidal amount of a 3,5-dihalogeno-1,2,6-thiadiazin-4-one of the formula I indicated in claim 1.

* * * * *